(12) United States Patent
Yin et al.

(10) Patent No.: US 12,324,790 B1
(45) Date of Patent: Jun. 10, 2025

(54) PREPARATION METHOD AND APPLICATION OF MICELLE PREPARATION CONTAINING THYMOL AND DERIVATIVE THEREOF

(71) Applicant: Nanjing Mucosa Tech Co., Ltd., Nanjing (CN)

(72) Inventors: Zhong Yin, Nanjing (CN); Wanzhou Zhao, Nanjing (CN)

(73) Assignee: NANJING MUCOSA TECH CO., LTD., Nanjing (CN)

( * ) Notice: Subject to any disclaimer, the term of this patent is extended or adjusted under 35 U.S.C. 154(b) by 0 days.

(21) Appl. No.: 18/974,530

(22) Filed: Dec. 9, 2024

(30) Foreign Application Priority Data

Jan. 22, 2024 (CN) .......................... 202410088884.4

(51) Int. Cl.
| | | |
|---|---|---|
| *A01N 43/00* | (2006.01) | |
| *A01N 43/46* | (2006.01) | |
| *A61K 9/107* | (2006.01) | |
| *A61K 31/05* | (2006.01) | |
| *A61K 31/55* | (2006.01) | |
| *A61K 47/22* | (2006.01) | |
| *A61K 47/26* | (2006.01) | |
| *A61P 1/04* | (2006.01) | |
| *C07D 311/72* | (2006.01) | |

(52) U.S. Cl.
CPC ............ *A61K 31/05* (2013.01); *A61K 9/1075* (2013.01); *A61K 47/22* (2013.01); *A61K 47/26* (2013.01); *A61P 1/04* (2018.01); *C07D 311/72* (2013.01)

(58) Field of Classification Search
None
See application file for complete search history.

(56) References Cited

FOREIGN PATENT DOCUMENTS

| | | |
|---|---|---|
| CA | 3197374 A1 | 5/2022 |
| CN | 1500524 A | 6/2004 |
| CN | 102139113 A | 8/2011 |
| CN | 104945538 A | 9/2015 |
| JP | 2023-168164 A | 11/2023 |

*Primary Examiner* — Layla Soroush
(74) *Attorney, Agent, or Firm* — Muncy, Geissler, Olds & Lowe. P.C.

(57) ABSTRACT

The present invention relates to a preparation method and application of a micelle preparation containing thymol and a derivative thereof. The micelle preparation contains thymol, a thymol derivative, a derivative (CST) formed by vitamin E and chondroitin sulfate, a derivative (TPGS) formed by vitamin E and polyethylene glycol, and water. On the one hand, the thymol is transformed into its derivative, so that the pungency degree of the thymol is effectively reduced, and the gasoline smell of the thymol is masked; on the other hand, the thymol and the derivative of the thymol are encapsulated by the vitamin E derivative to form micelles, so that the two components are effectively solubilized, and the biological adhesion of the micelle preparation is greatly enhanced. The micelle preparation can be used for oral ulcer treatment, oral care and correction of related oral cavity abnormalities.

3 Claims, 6 Drawing Sheets

PREPARATION METHOD AND APPLICATION OF MICELLE PREPARATION CONTAINING THYMOL AND DERIVATIVE THEREOF

TECHNICAL FIELD

The present invention relates to the field of natural medicines, in particular to a preparation method and application of a micelle preparation containing thymol and a derivative thereof.

BACKGROUND ART

Oral inflammatory diseases are common and frequent diseases in stomatology, with high clinical incidence and recurrence rates, such as pericoronitis, gingivitis, periodontitis and oral mucosal diseases. Oral ulcer is one of the most common oral mucosal diseases in clinical practice, manifested as obvious recurrent pain, and characterized by local redness, swelling and pain, affecting the patient's diet, pronunciation, swallowing and mood. The etiology of oral ulcer is unclear and caused by a variety of factors, such as immunity, genetics, systemic diseases, infection, tumor radiotherapy and chemotherapy, environment, etc. At present, there is no specific drug for the treatment of oral ulcer, but the elimination of inducements and symptomatic treatment are mostly used in clinical practice. At present, products used to relieve symptoms include stomatitis spray, dexamethasone acetate patch, Guilin watermelon frost, etc., all of which have certain therapeutic effects, but they all have their own obvious shortcomings.

Thymol (THY), CAS number 89-83-8, has antibacterial, antioxidant, anti-inflammatory and other activities. Because of the above-mentioned pharmacodynamic effects, THY has attracted attention in inhibiting inflammations of the oral mucosa. It has been reported in China that the combination of 0.25% domiphen and THY has shown good results in treating oral ulcer after chemotherapy (Shao Fang, Chinese Community Doctors (Medical Specialty). 2011, 13(12), 161). There are some traditional therapies abroad that use essential oils containing THY for the relief of oral ulcer, but no systematic studies. In addition, there have been studies abroad that have confirmed that THY has a therapeutic effect on ulcerative colitis models of animals, which also indirectly confirmed that THY has a relatively significant anti-inflammatory activity [Tahmasebi P, Abtahi Froushani S M, Afzale Ahangaran N. Thymol has beneficial effects on the experimental model of ulcerative colitis. Avicenna J Phytomed. 2019 November-December; 9(6):538-550].

THY has some problems in oral use, mainly because it presents poor water solubility and strong pungency, and strong gasoline smell. This necessitates the use of low-concentration THY in a THY-containing liquid preparation to reduce the pungency degree, the use of a certain concentration of organic solvent for solubilization, or the addition of surfactants such as Tween for solubilization, and the use of aromatic substances with strong smells (e.g., menthol, *eucalyptus* oil, etc.) to mask the taste of THY. The compliance of patients in the treatment of oral diseases with THY is improved to a certain extent, but needs to be further optimized: the organic solvent, menthol, *eucalyptus* oil, etc. contained in the solution may further irritate the oral ulcer surface, and the solution which contains a lower concentration of THY will also limit its efficacy.

SUMMARY OF THE INVENTION

The technical problem to be solved by the present invention is to overcome the defects of the existing THY liquid preparation, increase the solubility of THY, improve the efficacy of THY, increase the residence time of THY on the ulcer surface, reduce the pungency degree of THY, and mask the undesirable smell of THY. The present invention aims to prepare a preparation method and application of a micelle preparation containing thymol and a derivative thereof, in order to develop oral care and oral ulcer treatment products containing THY and/or a THY derivative suitable for use by people of different ages.

In order to solve the above-mentioned technical problems, the present invention provides the following technical solution: a compound, which is a thymol derivative, has a structural formula (I) as follows:

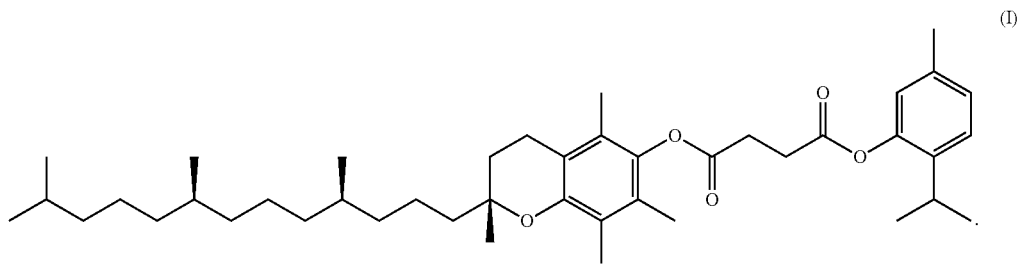 [SMILES: Cc1ccc(C(C)C)c(OC(=O)CCC(=O)Oc2c(C)c(C)c3c(c2C)CC[C@@](C)(CCC[C@H](C)CCC[C@H](C)CCCC(C)C)O3)c1]

In order to solve the above technical problem, the present invention provides a further technical solution: a micelle preparation. The preparation includes the following components in parts by weight:

Thymol (THY) 0.1 to 10 parts

Thymol derivative (THY-Tos) 0.1 to 10 parts

Derivative formed by vitamin E and chondroitin sulfate (CST) 0 to 10 parts

Derivative formed by vitamin E and polyethylene glycol (TPGS) 2 to 100 parts water 1000 parts, wherein a sum of masses of THY and THY-Tos in the micelle preparation does not exceed one-fifth of a sum of masses of CST and TPGS;

the THY-Tos has a structural formula (I) as follows:
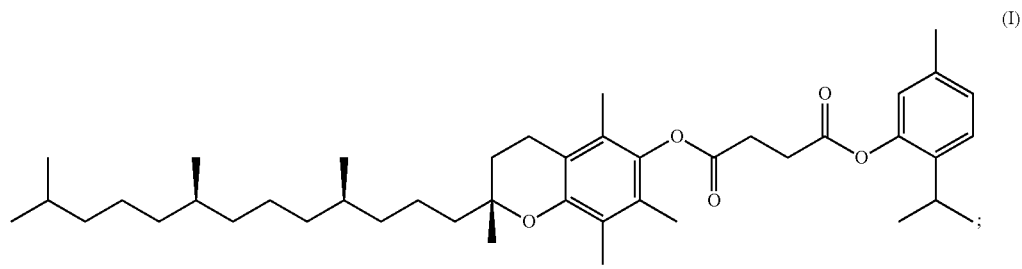 [SMILES: Cc1ccc(C(C)C)c(OC(=O)CCC(=O)Oc2c(C)c(C)c3c(c2C)CC[C@@](C)(CCC[C@H](C)CCC[C@H](C)CCCC(C)C)O3)c1]
the THY has a structural formula (II) as follows:
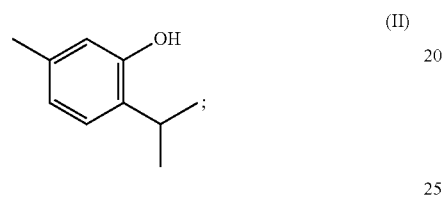
the CST has a structural formula (III) as follows:
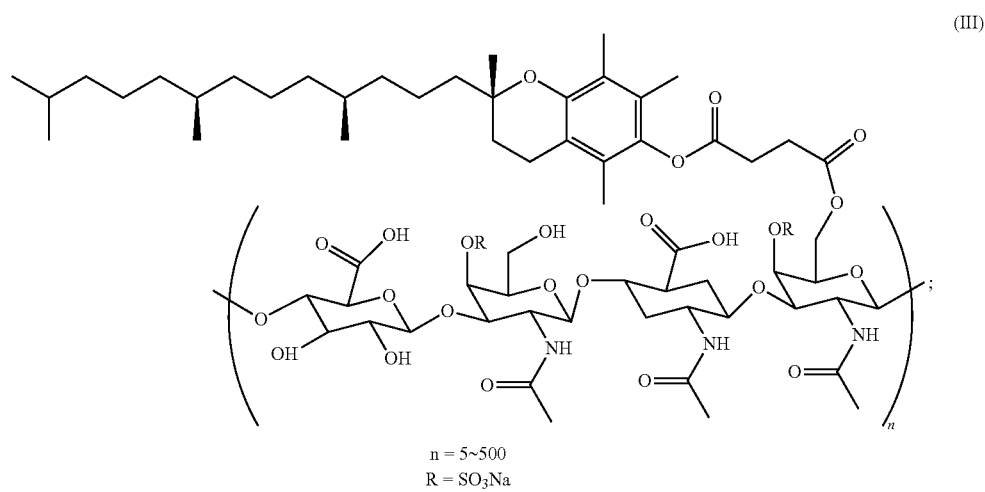
n = 5~500
R = SO$_3$Na
the TPGS has a structural formula (IV) as follows:
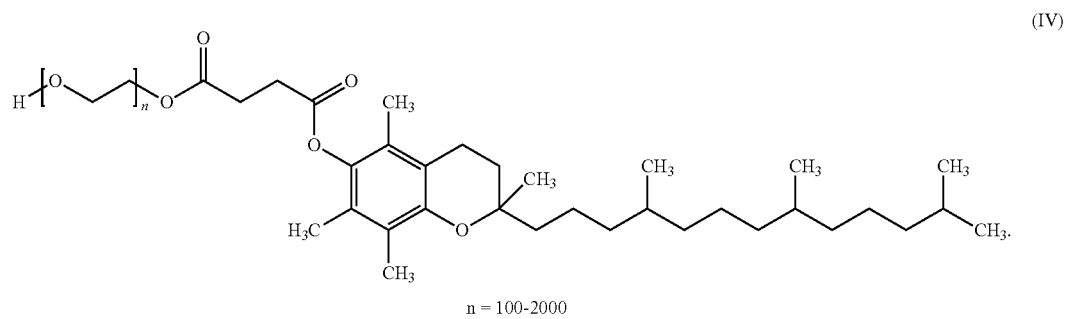
n = 100-2000

Preferably, the micelle preparation contains the following components in parts by mass:
THY 0.2 to 6 parts
THY-Tos 0.2 to 6 parts
CST 0.1 to 5 parts
TPGS 2 to 120 parts
purified water 1000 parts.

Preferably, the micelle preparation contains the following components in parts by mass:
THY 1 to 3 parts
THY-Tos 1 to 3 parts
CST 0.2 to 3 parts
TPGS 10 to 90 parts
purified water 1000 parts.

Preferably, the micelle preparation contains the following components in parts by mass:
THY 1 part
THY-Tos 1 part
CST 2 parts
TPGS 28 parts
purified water 1000 parts.

Preferably, the micelle preparation further contains one or more polymer materials selected from the group consisting of carbomer, sodium carboxymethyl cellulose, methyl cellulose, hydroxyethyl cellulose, hydroxypropyl cellulose, hydroxypropyl methyl cellulose.

In order to solve the technical problems of the present invention, a further technical solution provided by the present invention is an application of the micelle preparation, wherein the micelle preparation is used to prepare drugs, medical devices or other oral care products for treating oral ulcer.

The Present Invention has the Following Beneficial Effects

We stumbled upon an interesting finding in our preliminary work that when THY and vitamin E were used together on an animal model of oral ulcer, better therapeutic effects were achieved than when either THY or vitamin E was used alone.

Based on the above finding, on the one hand, we esterify THY with vitamin E succinate (Tos) to form a THY derivative (THY-Tos). It is surprised to find that the efficacy of THY-Tos on an animal-based oral ulcer model is not significantly different from that of using THY in combination with vitamin E. We are also pleasantly surprised to find that the pungency and gasoline smell of THY-Tos virtually disappears, which is beneficial for improving the patients' compliance.

Given that the solubility of THY and THY-Tos is not high, on the other hand, from the perspective of a therapeutic drug carrier, we form a chondroitin sulfate derivative (CST) by esterifying chondroitin sulfate (CS) with Tos, which are spontaneously formed into a micelle preparation at room temperature. Further, we stumbled upon an unexpected finding that a water-soluble derivative of natural vitamin E, D-α-tocopherol polyethyleneglycol 1000 succinate (TPGS), is mixed with CST to form a mixed micelle (CST/TPGS) at room temperature in water. In addition, a critical micelle concentration (CMC) of the mixed micelle is lower than that formed by CST alone, which makes the CST/TPGS mixed micelle more stable in terms of physical structure. We find that the CST/TPGS micelle has good encapsulation and solubilization effects on THY and THY-Tos, and the formed THY micelle, or THY-Tos micelle, or mixed micelle of THY and THY-Tos can all increase the solubility of THY or THY-Tos and have good stability. Furthermore, we are pleasantly surprised to find that the drug-loaded CST/TPGS micelle preparation exhibits good bioadhesive properties. If the mixed micelle carrier is encapsulated with THY, or with THY-Tos, or with a mixture of THY and THY-Tos, after the preparation is allowed to retain in the mucous membrane tissue for a certain period of time, it is found that more drug is retained on the mucous membrane, which is beneficial for the drug to stay in the oral ulcer site for a longer period of time. Furthermore, by adding a certain concentration of high molecular materials (such as carbomer, carboxymethyl cellulose, hydroxypropyl methylcellulose, and hydroxyethyl cellulose) to the CST/TPGS-loaded micelle preparation, the viscosity of the liquid micelle preparation is increased, making it convenient to use.

DETAILED DESCRIPTION OF THE INVENTION

Figure 1:
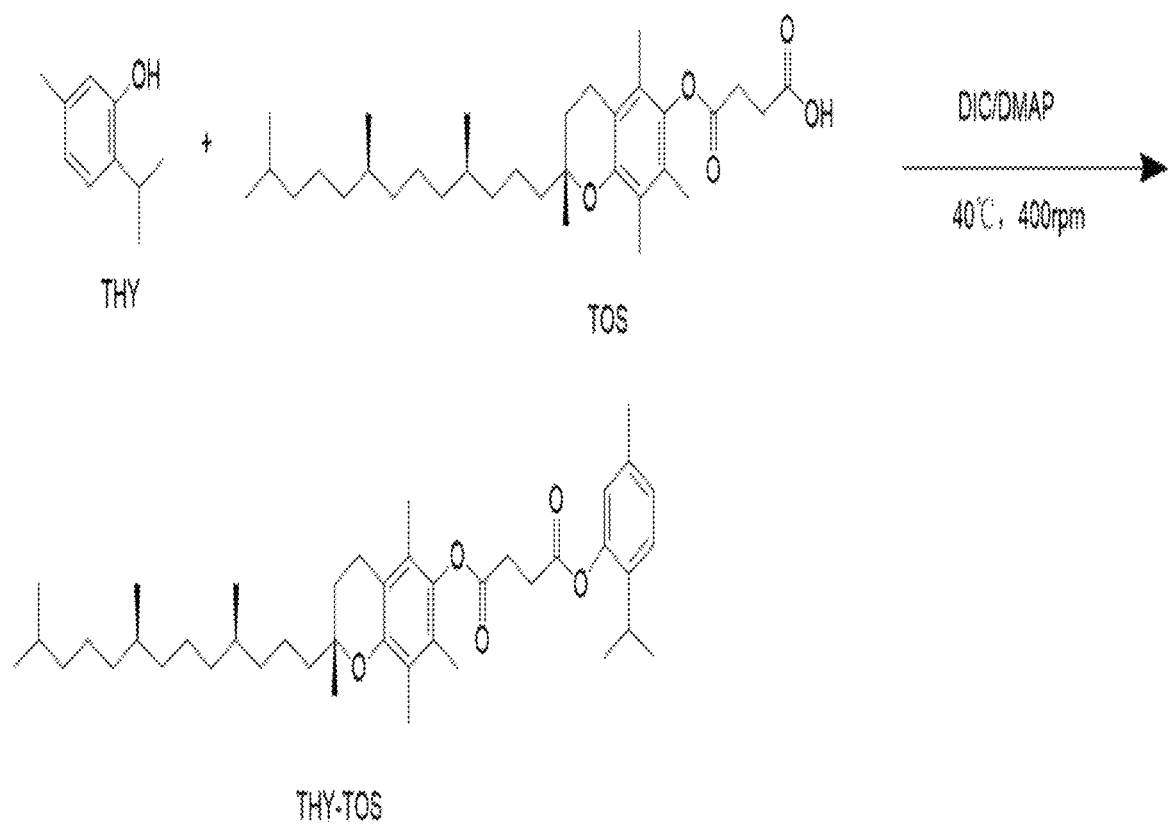
FIG. 1 is a synthesis route diagram of THY-Tos.

The present invention will be further described below in conjunction with the accompanying drawings. The preferred embodiments of the present invention are described below. It should be understood that the preferred embodiments described here are only used to describe and explain the present invention, but not used to limit the present invention.

Example 1: THY Aqueous Solution

THY has poor solubility in water. It was reported that its solubility in water at 25° C. was less than 1 mg/ml (https://echa.europa.eu/registration-dossier/-/registered-dossier/11030/4/1). THY aqueous solutions at low, medium, and high concentrations were prepared at room temperature for subsequent comparison and evaluation with micelle preparations. Preparation method: an appropriate amount of THY raw material was added to a beaker, added with 50 mL of water, and magnetically stirred at room temperature for 72 h to form THY aqueous solutions having concentrations 0.1, 0.5, and 0.9 mg/ml, respectively.

TABLE 1

| THY aqueous solutions | |
| --- | --- |
| Solution No. | Solution concentration (mg/ml) |
| 1 (low concentration) | 0.1 |
| 2 (medium concentration) | 0.5 |
| 3 (high concentration) | 0.9 |

Example 2: TPGS Micelle Preparations of THY

THY has poor water solubility and can be solubilized by adding with an organic solvent or adding with a surfactant. A surfactant TPGS was selected for solubilization. Preparation method: 40 mg of THY was weighed and placed in a beaker, added with a certain amount of water and TPGS and magnetically stirred at room temperature for 24 h. In micelle preparations 2-8, mass ratios of THY to TPGS were 2:1, 1:1, 1:2.5, 1:5, 1:7, 1:10, 1:15, and 1:20, respectively. The states of the above micelle preparations were observed with the naked eyes.

TABLE 2

TPGS micelle preparations of THY

| Preparation No. | THY (mg) | TPGS (mg) | Water (mL) | Preparation states |
|---|---|---|---|---|
| 1 | 40 | 0 | 20 | Turbid liquid |
| 2 | 40 | 20 | 20 | Milk white turbid liquid |
| 3 | 40 | 40 | 20 | Milk white turbid liquid |
| 4 | 40 | 100 | 20 | Milk white liquid |
| 5 | 40 | 200 | 20 | Milk white liquid |
| 6 | 40 | 280 | 20 | Light blue opalescent, semi-transparent liquid |
| 7 | 40 | 400 | 20 | Light blue opalescent, transparent liquid |
| 8 | 40 | 600 | 20 | Light blue opalescent, transparent liquid. |
| 9 | 40 | 800 | 20 | Light blue opalescent, transparent liquid. |

This study indicated that when the apparent concentration of THY was 2 mg/ml, the TPGS-free preparation was in a turbid state and had precipitations, indicating that THY had poor water solubility. As TPGS was gradually added, the preparation system became milky white until it became semi-transparent and transparent, indicating that TPGS had a good solubilization effect on THY. In particular, when a mass ratio of THY to TPGS was 1:7 or TPGS has a larger proportion, the solubilization effect was better, and the micelle system was stable.

Example 3: Formation of THY-Tos by Esterification of THY and Tos

Tos (100 mg) was dissolved in 5 mL of dichloromethane (DCM), followed by addition of dicyclohexylcarbodiimide (DCC, 46.65 mg) and 4-dimethylaminopyridine (DMAP, 2.3 mg). The mixture was stirred at room temperature for 2 h to obtain a solution A. The solution A was added dropwise to 2 mL of DCM solution containing THY (42.45 mg), and reacted at 40° C. for 36 h. The reaction solution was dried by rotary evaporation under reduced pressure. The residue was separated by column chromatography to obtain 63 mg of colorless oily product THY-Tos with a yield of 50%. The synthesis of THY-Tos was shown in FIG. 1.

Figure 2:
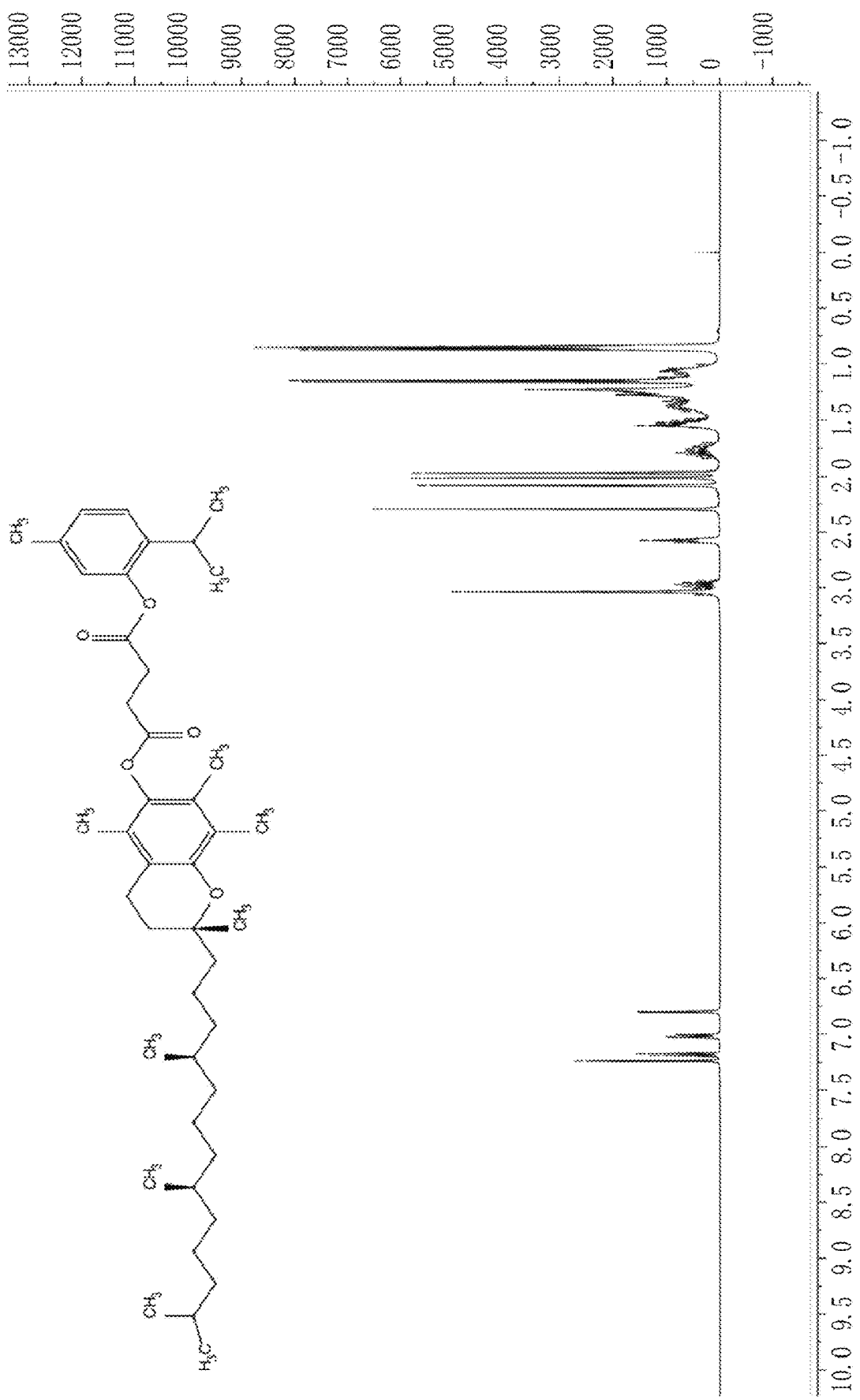
FIG. 2 is an NMR hydrogen spectrum of THY-Tos.

An NMR hydrogen spectrum ($^1$H-NMR) of THY-Tos and its attribution diagram were shown in FIG. 2. $^1$H NMR (400 MHz, Chloroform-d) δ 7.21 (d, J=7.9 Hz, 1H, H-3'), 7.05 (dd, J=8.0, 1.8 Hz, 1H, H-4'), 6.83 (d, J=1.7 Hz, 1H, H-6'), 3.07 (s, 4H, H-11, H-12), 3.00 (m, 1H, H-7'), 2.61 (t, J=6.8 Hz, 2H, H-7), 2.32 (s, 3H, Ar—CH$_3$), 2.11 (s, 3H, Ar—CH$_3$), 2.04 (s, 3H, Ar—CH$_3$), 2.00 (s, 3H, Ar—CH$_3$), 1.89-1.73 (m, 2H, H-6), 1.64-1.47 (m, 4H), 1.46-1.25 (m, 14H), 1.19 (d, J=6.9 Hz, 6H, 7'-CH$_3$, 7'-CH$_3$), 1.17-1.02 (m, 6H), 0.93-0.84 (m, 12H, Aliphatic-CH$_3$).

Example 4 TPGS Micelle Preparations of THY-Tos

A preparation method of TPGS micelle preparations of THY-Tos was similar to the preparation method of the THY micelle preparation in Example 2. 40 mg of THY-Tos was weighed and placed in a beaker, and added with a certain amount of water and TPGS. For Preparations 2 to 5, the mass ratios of THY-Tos to TPGS were 1:1, 1:7, 1:10, and 1:15, respectively. The above micelle preparations were magnetically stirred for 24 h to obtain the final products. The states of the micelle preparations were observed with the naked eyes.

TABLE 3

TPGS micelle preparation of THY-Tos

| Preparation No. | THY-Tos (mg) | TPGS (mg) | Water (mL) | Preparation states |
|---|---|---|---|---|
| 1 | 40 | 0 | 20 | Turbid liquid |
| 2 | 40 | 40 | 20 | Milk white turbid liquid |
| 3 | 40 | 280 | 20 | Light blue opalescent, semi-transparent liquid. |
| 4 | 40 | 400 | 20 | Light blue opalescent, transparent liquid. |
| 5 | 40 | 600 | 20 | Light blue opalescent, transparent liquid. |

This study indicated that THY-Tos also had poor solubility, but TPGS could effectively improve the solubility of THY-Tos. In particular, when the mass ratio of THY to TPGS was 1:7 or TPGS had a larger proportion, the solubilization effect was better, and the micelle system was stable.

Example 5: Synthesis of CST by Esterification of CS and Tos

Figure 3:
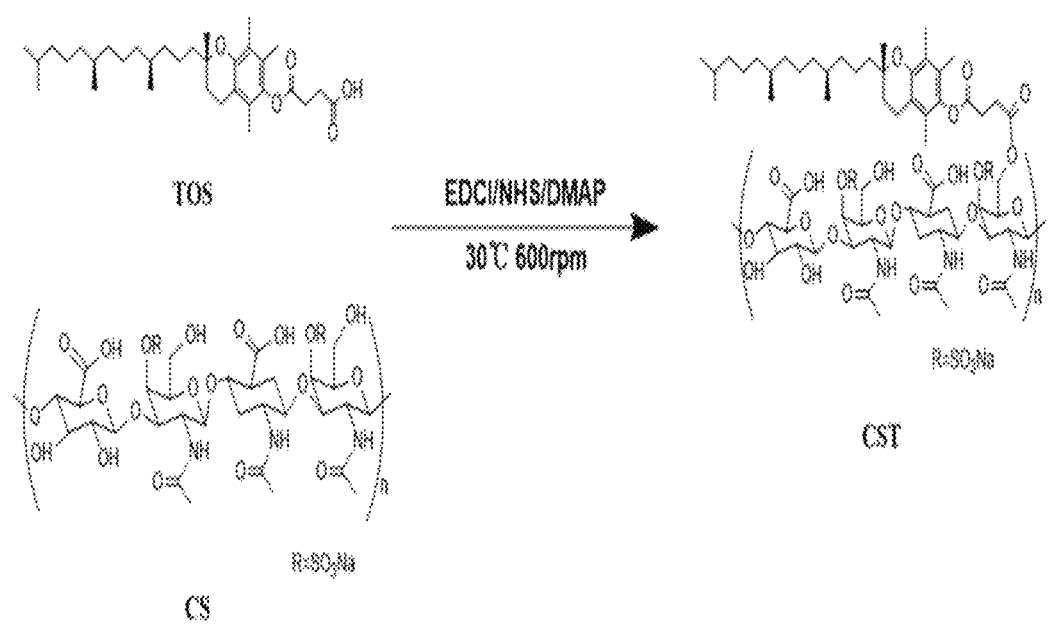
FIG. 3 is a synthesis route diagram of CST.
Figure 4A:
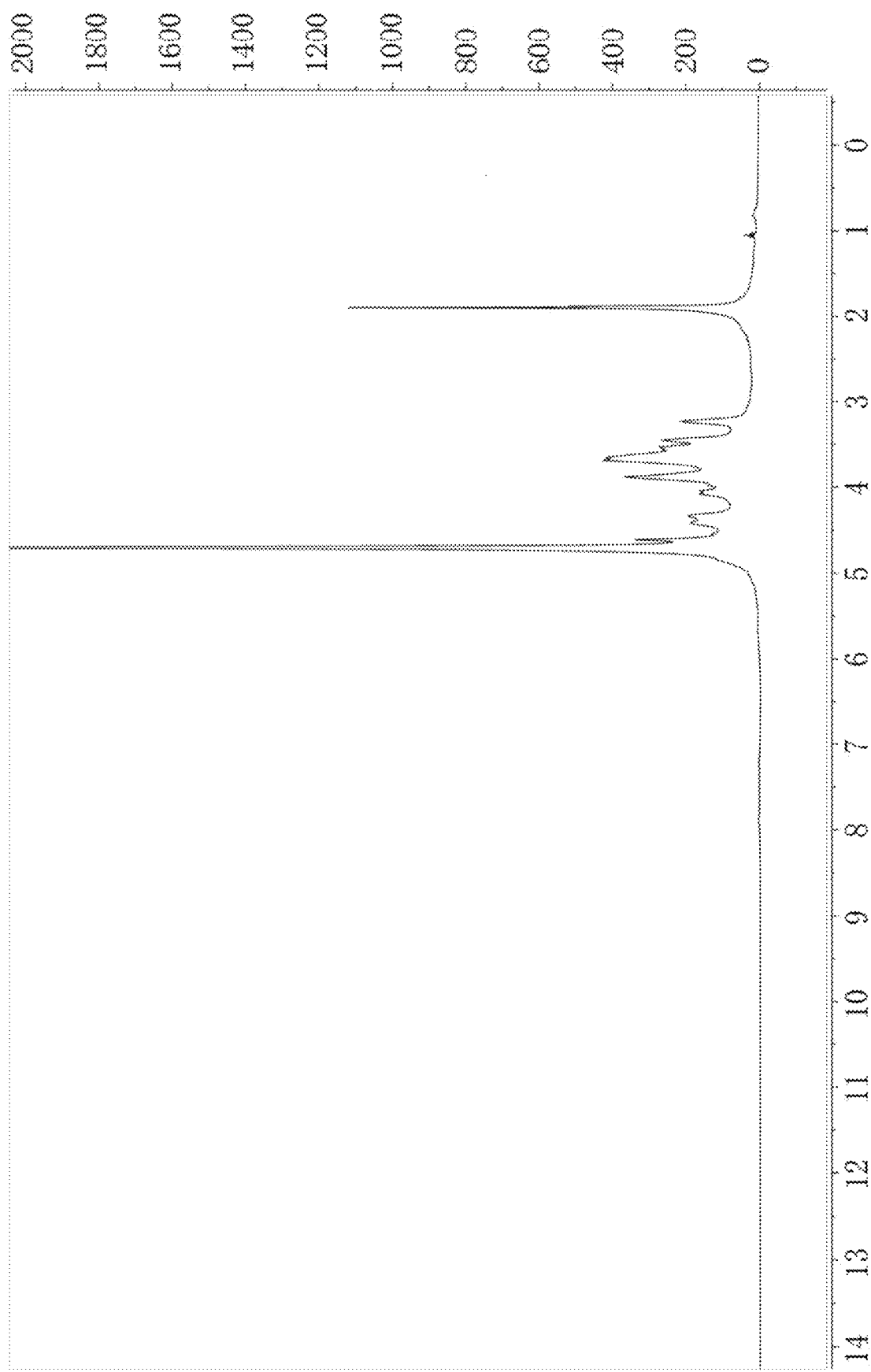
FIGS. 4a, 4b, and 4c are NMR hydrogen spectra of CS, Tos and CST, respectively.
Figure 4B:
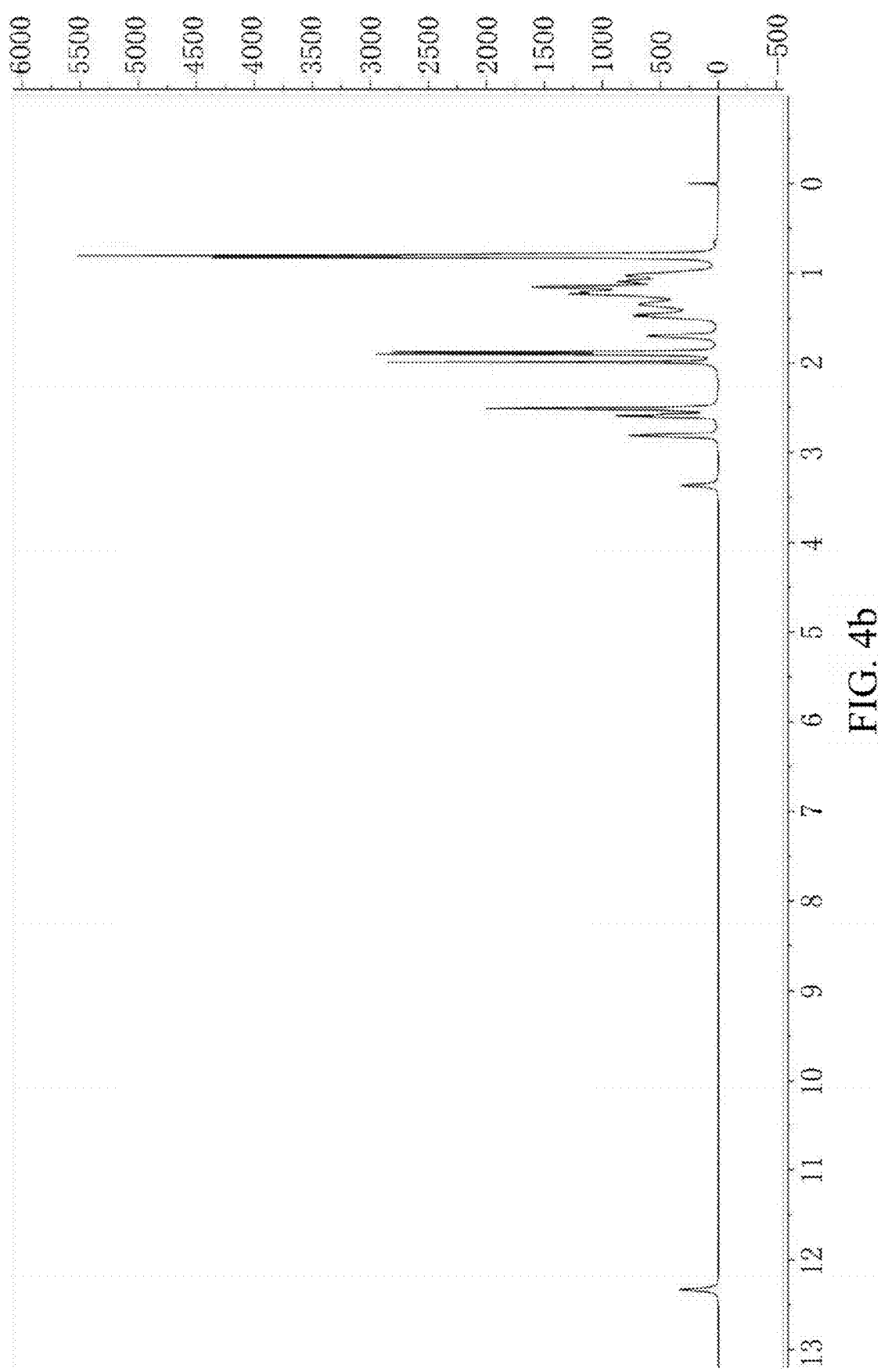
Figure 4C:
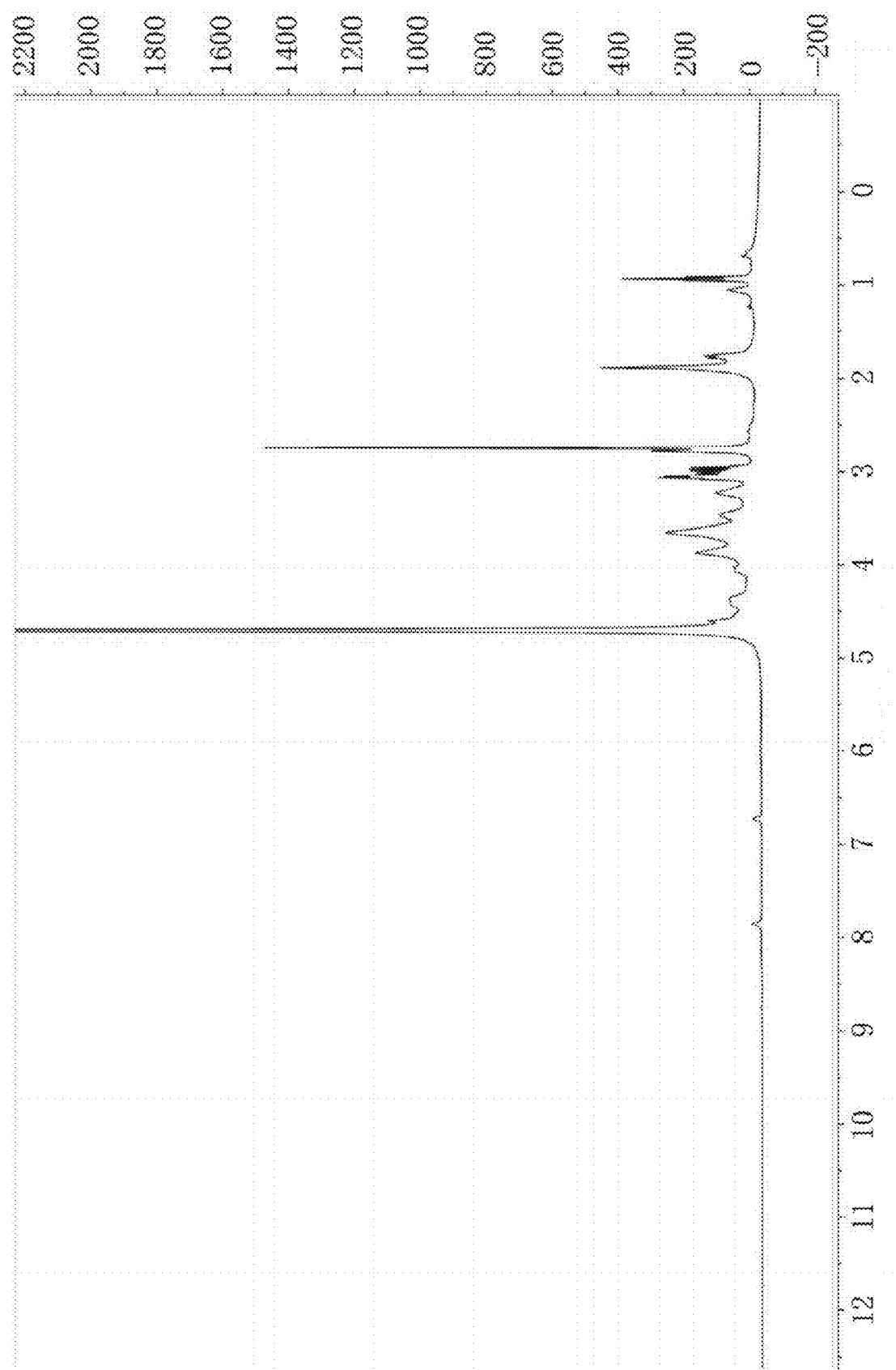

Tos (796.17 mg), 1-ethyl-(3-dimethylaminopropyl) carbodiimide hydrochloride (EDCI, 0.5751 g), N-hydroxysuccinimide (NHS, 0.3453 g), and DMAP (85.52 mg) were added to N,N-dimethylformamide (DMF, 12 mL) and stirred at 30° C. for 3 h to activate carboxyl group of Tos. CS (530.78 mg) in DMF (6 mL) was slowly added to the activated Tos solution. The reaction solution was continuously stirred at 30° C. for 48 h. The solution was precipitated with cold acetone to remove excess Tos. The precipitate was dissolved in pure water, and then dialyzed (molecular weight cutoff: 3.5 kDa) to remove the catalyst and the solvent, and the product was finally lyophilized to obtain the final product. The synthesis route of CST was shown in FIG. 3. NMR hydrogen spectra of CS, Tos and CST were shown in FIG. 4.

According to $^1$H-NMR, a characteristic peak of Tos appeared on the spectrum of the dialyzed and purified CST, indicating that the Tos was linked to CS through esterification.

Example 6: Preparation of CST/TPGS Mixed Preparation of THY and/or THY-Tos

An appropriate amount of THY, THY-Tos, or THY in combination with THY-Tos was mixed with an appropriate amount of CST and TPGS, stirred and dissolved with 50 ml of absolute ethanol until clarified, and an organic solvent was removed by rotary evaporation. 5 mL of water was added to this flask and shaken to fully hydrate a film on the wall of the flask. Ultrasonic treatment was performed (100 W, 5 s/5 s, 10 min) to obtain 5 mL of light blue opalescent solution.

TABLE 4

CST/TPGS micelle solutions of THY and/or THY-Tos

| Solution No. | THY (mg) | THY-Tos (mg) | CST (mg) | TPGS (mg) | Solution state |
|---|---|---|---|---|---|
| 1 | 10 | 0 | 10 | 60 | All were clear micelle solutions with light blue opalescence |
| 2 | 7.5 | 2.5 | 10 | 60 | |
| 3 | 5 | 5 | 10 | 60 | |
| 4 | 2.5 | 7.5 | 10 | 60 | |
| 5 | 0 | 10 | 10 | 60 | |
| 6 | 5 | 5 | 10 | 40 | |
| 7 | 5 | 5 | 10 | 90 | |
| 8 | 5 | 5 | 10 | 140 | |
| 9 | 5 | 5 | 10 | 190 | |
| 10 | 5 | 5 | 1 | 50 | |
| 11 | 15 | 15 | 15 | 450 | |
| 12 | 5 | 15 | 1 | 450 | |
| 13 | 15 | 5 | 15 | 50 | |

This study indicated that CST and TPGS formed a mixed micelle and successfully solubilized THY and/or THY-Tos. In addition, the mixed micelle formed by CST and TPGS had better solubilization ability than a TPGS micelle. This was manifested: when a ratio of the total mass of THY and THY-Tos to the total mass of CST and TPGS was 1:7, the formed system was a clear micelle solution system with light blue opalescence. However, through Example 2 and Example 4, it can be seen that when a ratio of the mass of THY or THY-Tos to the mass of TPGS is 1:7, the system was not completely clear but showed semi-transparent characteristics. Further, according to an experiment of Solution 6 in this example, we were also pleasantly surprised to find that even when a ratio of the total mass of THY and THY-Tos to the total mass of CST and TPGS was 1:5, a clear micelle solution system with light blue opalescence could still be formed, which fully demonstrated its stronger solubilization ability.

Example 7: Comparison of Pungency Degrees

Six volunteers with good health and good sense of smell and taste sensitivity (a ratio of men to women was 1:1) were selected to taste and score some of the preparations in Examples 1, 2, 4 and 6, and each volunteer scored the micelle solutions individually. The evaluation criteria were shown in Table 5. The scores of all volunteers' taste were recorded, and statistical average values were used as sensory evaluation results.

TABLE 5

Taste scoring criteria

| Taste | Scores |
|---|---|
| Extremely pungent and difficult to accept | 0 |
| Pungent, reluctant or unwilling to accept | 1 |
| Little pungent and basically acceptable | 2 |
| Slightly pungent and acceptable | 3 |
| Not pungent | 4 |

TABLE 6

Pungency degree test of respective solutions and preparations

| Test solutions | Volunteer 1 | Volunteer 2 | Volunteer 3 | Volunteer 4 | Volunteer 5 | Volunteer 6 | Averaged pungency degree |
|---|---|---|---|---|---|---|---|
| Solution 1 in Example 1 | 0 | 1 | 1 | 1 | 0 | 1 | 0.67 |
| Solution 3 in Example 1 | 0 | 0 | 0 | 0 | 0 | 0 | 0.00 |
| Preparation 6 in Example 2 | 1 | 1 | 2 | 1 | 0 | 1 | 1.00 |
| Preparation 7 in Example 2 | 1 | 2 | 3 | 2 | 1 | 2 | 1.83 |
| Preparation 8 in Example 2 | 3 | 3 | 4 | 3 | 3 | 3 | 3.17 |
| Preparation 9 in Example 2 | 3 | 4 | 4 | 4 | 3 | 4 | 3.67 |
| Preparation 3 in Example 4 | 4 | 4 | 4 | 4 | 4 | 4 | 4.0 |
| Preparation 1 in Example 6 | 3 | 4 | 4 | 4 | 3 | 4 | 3.67 |
| Preparation 3 in Example 6 | 4 | 4 | 4 | 4 | 4 | 4 | 4.00 |
| Preparation 5 in Example 6 | 4 | 4 | 4 | 4 | 4 | 4 | 4.00 |
| Preparation 6 in Example 6 | 4 | 4 | 4 | 4 | 3 | 4 | 3.83 |
| Preparation 8 in Example 6 | 4 | 4 | 4 | 4 | 4 | 4 | 4.00 |
| Preparation 9 in Example 6 | 4 | 4 | 4 | 4 | 4 | 4 | 4.00 |

This study indicated that when THY was dissolved in water as a pure solution, it had a strong pungent taste at both low (0.1 mg/ml) and high concentrations (0.9 mg/ml). Especially for THY aqueous solutions at high concentrations, all the volunteers found the pungent degree was difficult to accept. After THY was prepared into a TPGS micelle solution, the pungency degree decreased. In particular, when a mass ratio of THY to TPGS was 1:10, or TPGS had a larger proportion, the pungency degree significantly decreased, which was reflected in all volunteers.

On the other hand, when THY was esterified with Tos, the pungency degree of the formed THY-Tos all disappeared. It should be noted that when THY-Tos was absorbed into the oral mucosa, abundant hydrolytic enzymes present in the oral tissues could theoretically hydrolyze ester bonds formed by the combination of THY and Tos, so that THY and Tos were released. Further, Tos could also be further hydrolyzed to form vitamin E, so that THY and vitamin E could synergistically intervene in oral ulcer and promote wound healing.

Hydrolysis of THY-Tos took time. If a THY-Tos micelle was used alone on a wound surface, although THY was released in a controlled manner within a tissue inside the wound surface, THY, if contained in the preparation at the same time, can contribute to a faster onset of action at the beginning of the medication. Therefore, we loaded THY and THY-Tos together into a CST/TPGS mixed micelle and confirmed through volunteers' attempts to taste each mixed micelle that the pungency degree significantly decreased. One reason for the decrease in pungency degree was that the micelle contained both non-pungency THY-Tos and lower-concentration THY, while the other reason was attributed to the effective wrapping of THY and THY-Tos by CST/TPGS.

Example 8: Comparison of Bioadhesive Properties

The bioadhesive properties of the preparations in some embodiments were evaluated by an ex vivo intestinal perfusion method for rats. Sprague Dawley male and female rats (each having body mass of 220 g±20 g) were divided into 7 groups, 10 rats in each group. After the sacrifice, the colons were removed and cut down along the cecum. The content was rinsed off with pH 7.4 phosphate buffer and attached to an inclined fixed tube. 10 ml of each of the preparations in some embodiments in the following table was added dropwise from the upper mouth of the inclined tube, and each eluted preparation was received with a beaker at the lower mouth of the inclined tube, and slowly added dropwise for 5 min. After the dropwise addition, 20 ml of pure water was added dropwise from the upper mouth of the inclined tube again, and all eluents were received with the same beaker, and each added dropwise for 10 min. Methanol was added to the eluted solution to a fixed volume of 50 ml, shaken for 24 h, and centrifuged. The supernatant was taken. THY was quantified by HPLC-UV. A bioadhesion rate was calculated according to the following formula.

Bioadhesion rate=$(n_1-n_2)n_1 \times 100\%$.

In the formula, $n_1$ was the THY content in 10 ml of test sample before perfusion, and $n_2$ was the THY content in the eluted solution.

TABLE 7

Bioadhesive property tests for respective preparations

| Test solutions | Bioadhesion rate (%) |
| --- | --- |
| Solution 1 in Example 1 | 9.3 |
| Solution 3 in Example 1 | 8.1 |
| Preparation 7 in Example 2 | 23.0 |
| Preparation 8 in Example 2 | 25.8 |
| Preparation 9 in Example 2 | 26.3 |
| Preparation 5 in Example 4 | 26.0 |
| Preparation 1 in Example 6 | 58.7 |
| Preparation 3 in Example 6 | 60.1 |
| Preparation 5 in Example 6 | 64.3 |
| Preparation 6 in Example 6 | 59.8 |

TABLE 7-continued

Bioadhesive property tests for respective preparations

| Test solutions | Bioadhesion rate (%) |
| --- | --- |
| Preparation 8 in Example 6 | 71.2 |
| Preparation 9 in Example 6 | 73.8 |

This example attempted to evaluate the bioadhesive property of each preparation with the intestinal mucosa instead of the buccal mucosa. Obviously, if a preparation had good bioadhesive property, it would be retained by the mucosa at a higher proportion as it passed through the rat intestine. The two solutions in Example 1 were both simple aqueous solutions of THY and did not possess obvious bioadhesive properties. The two solutions in Example 2 were TPGS micelle preparations of TY and, due to the presence of polyethylene glycol (PEG) chain segments in TPGS, exhibited certain bioadhesive properties. Several solutions in Example 6 were mixed micelle solutions of THY and THY-Tos, showing obvious bioadhesive properties. In particular, when ratios of the total mass of THY and THY-Tos to the total mass of CST and TPGS were 1:15 (Solution 8 in Example 6) and 1:20 (Solution 9 in Example 6), their bioadhesion rates were both more than 70%. The bioadhesive property of the CST/TPGS mixed micelle preparation was significantly better than that of a micelle preparation composed of TPGS alone.

Example 9: Increase in the Viscosity of Preparations

Thickening preparations were prepared. Preparation method: various substances were weighed according to the following table, placed in a beaker, and added with water to the full amount. All the substances were magnetically stirred for 24 h to obtain the final product. An NDJ-5S rotational viscometer (Shanghai Changji Geological Instrument Co., Ltd.) with No. 2 rotor was used to determine the viscosity of each preparation.

TABLE 8

Viscosity test of thickening preparations

| Preparation No. | THY (mg) | THY-Tos (mg) | TPGS (mg) | Sodium carboxy-methyl cellulose (%) | Water | Viscosity (mPa · s) |
| --- | --- | --- | --- | --- | --- | --- |
| 1 | 40 | 0 | 600 | 0 | 20 ml | Not detachable |
| 2 | 40 | 0 | 600 | 0.06 | 20 ml | 16 |
| 3 | 40 | 0 | 600 | 1 | 20 ml | 405 |
| 4 | 40 | 0 | 600 | 2 | 20 ml | 1289 |
| 5 | 20 | 20 | 600 | 2 | 20 ml | 1320 |

As can be seen from the above table, when sodium carboxymethyl cellulose was not added, the viscosity of the preparation was very low, resulting in easy loss of a liquid medicine because of high fluidity of the preparation itself when the preparation was applied to an affected area. After sodium carboxymethyl cellulose was added to the preparation system, the viscosity of the preparation increased with the increase of the concentration of sodium carboxymethyl cellulose. When a preparation with a certain viscosity was used in the affected area of the oral cavity, the fluidity of a liquid medicine was lower, which was good to improving the compliance of the patient in use.

Example 10: Pharmacodynamic Studies (1) Drug Preparation Method (I) 0.05% THY aqueous solution group: prepared according to the method shown in Example 1, and the THY concentration in the final solution was 0.5 mg/ml (Solution 2 in Example 1).

(II) 0.05% THY and 0.05% vitamin E aqueous solution group: preparation method: an appropriate amount of THY raw material and vitamin E raw material were added to a beaker, added with 50 mL of water (containing ethanol and PEG400 with volume fractions of 10% and 5%, respectively), and magnetically stirred at room temperature for 72 h, and the concentrations of THY and vitamin E in the final solution were 0.5 mg/ml, respectively.

(III) 0.05% THY-Tos aqueous solution group: preparation method: an appropriate amount of THY-Tos was added to a beaker, added with 50 mL of water (containing ethanol and PEG400 with volume fractions of 10% and 5%, respectively), and magnetically stirred at room temperature for 72 h, and the concentration of THY-Tos in the final solution was 0.5 mg/ml.

(IV) TPGS micelle preparation group of 0.2% THY: prepared according to the method shown in Example 2, and the THY concentration in the preparation was 2 mg/ml (Solution 8 in Example 2).

(V) Thickened TPGS micelle preparation group of 0.2% THY: prepared according to the method shown in Example 9, and the THY concentration in the preparation was 2 mg/ml (Solution 2 in Example 9).

(VI) CST/TPGS mixed micelle preparation group of 0.2 THY: prepared according to the method shown in Example 6, and the THY concentration in the preparation was 2 mg/ml (Solution 1 in Example 6).

(VII) CST/TPGS mixed micelle preparation group of 0.2% THY-Tos: prepared according to the method shown in Example 6, and the THY concentration in the preparation was 2 mg/ml (Solution 5 in Example 6).

(VIII) CST/TPGS mixed micelle preparation group of 0.1% THY and 0.1% THY-Tos: prepared according to the method shown in Example 6, and the concentrations of THY and THY-Tos in the preparation were 1 mg/ml (Solution 8 in Example 6), respectively.

(2) Animals

Source, germline, strain: SPF-grade SD rats, provided by Beijing Vital River Laboratory Animal Technology Co., Ltd. Laboratory animal production license: SCXK (Su) 2019-0001; Laboratory animal use license: SYXK (Su) 2021-0086; Animal weight: 180-220 g; Animal gender: half male and half female.

(3) Experimental Instruments

DK-8D Constant Temperature Water Bath, Shanghai Jinghong Experimental Equipment Co., Ltd.; Sartorius Electronic Balance, Sartorius Scientific Instruments (Beijing) Co., Ltd.

(4) Experimental Method

After 3 days of adaptive feeding, each rat was anesthetized and fixed on an operating table, the labial mucosa of the SD rat was dried with sterile cotton balls, and further sterile cotton balls were used for moisture isolation. A 3 mm×3 mm NaOH crystal was placed on the labial mucosa, and then removed after being maintained for 30 s. A treated area was wiped with sterile cotton balls containing normal saline to remove residual NaOH. After modeling was completed, the rates were randomly divided into a normal group, a model group, a 0.05% THY aqueous solution (once daily) group, a 0.05% THY aqueous solution (three times daily) group, a 0.05% THY and 0.05% vitamin E aqueous solution (once daily) group, a 0.05% THY-Tos aqueous solution (once daily) group, a 0.2% THY micelle preparation (once daily) group, a 0.2% THY micelle preparation (three times daily) group, a thickened 0.2% THY TPGS micelle preparation (once daily) group, a thickened 0.2% THY TPGS (twice daily) group, a 0.2% THY CST/TPGS mixed micelle preparation (once daily) group, a 0.2% THY-Tos CST/TPGS mixed micelle preparation (once daily) group, a 0.1% THY and 0.1% THY-Tos CST/TPGS mixed micelle preparation (once daily) group, a Guilin Watermelon Frost (once daily) group, and a Guilin Watermelon Frost (three times daily) group. The Guilin Watermelon Frost group was externally applied to a wound surface for 9 days, and the other administration groups were instilled 9 times for 9 days, respectively. The control group and the model group were administrated with normal saline by gavage, respectively.

An area method was used to macroscopically evaluate the oral ulcer area, a maximum transverse diameter and longitudinal diameter of the ulcer were measured by vernier calipers, which were marked as $d_1$ and $d_2$, respectively, and a ulcer area was $S=\pi \times d_1 \times d_2 \times \frac{1}{4}$ ($\pi=3.14$).

Ulcer area inhibition rate=(1−mean ulcer area in the administration group/mean ulcer area in the model group)×100%.

(5) Statistical Method

The analysis was performed by t-test, and normally distributed quantitative data were expressed as mean±standard deviation ($\overline{X}$, ±S), one-way ANOVA and LSD methods were used for pairwise comparison, and the Wilcoxon rank-sum test was used when the ANOVA conditions were not met. If $\alpha=0.05$, $P<0.05$ indicated a statistical difference, $P<0.01$ indicated a significant statistical difference, and $P>0.05$ indicated no statistical difference.

(6) Effects of Respective Drug Preparations on the Oral Mucosa of Rats in Respective Groups After 9 days of administration in each group, ulcer surfaces were visible to the naked eyes in the model group, the 0.05% THY aqueous solution (once daily) group, the 0.2% THY micelle solution (once daily) group, and the Guilin Watermelon Frost (once daily) group; slight ulcers were visible to the naked eyes in the 0.05% THY aqueous solution (three times daily) group, the thickened 0.2% THY TPGS micelle solution (once daily) group, and the Guilin Watermelon Frost (three times daily) group; and there was no obvious ulcer surface in the other administration groups.

TABLE 8

Effects of THY preparation on ulcer area and ulcer inhibition rate in oral ulcer rats ($\overline{X}$ ± SD, n = 10, ulcer area unit: mm$^2$)

| Groups | 1 d Ulcer area | 9 d Ulcer area | Inhibition rate % |
|---|---|---|---|
| Model group | 18.8 ± 3.1 | 18.1 ± 3.0 | — |
| 0.05% THY aqueous solution (once daily) group | 19.1 ± 2.1 | 5.5 ± 0.9** | 69.8 |
| 0.05% THY aqueous solution (three times daily) group | 18.9 ± 3.3 | 2.2 ± 0.4** | 87.7 |
| 0.05% THY and 0.05% vitamin E aqueous solution (once daily) group | 18.5 ± 2.4 | 3.5 ± 1.2** | 80.1 |
| 0.05% THY-Tos aqueous solution (once daily) group | 18.9 ± 2.9 | 3.4 ± 1.0** | 81.3 |
| 0.2% THY micelle preparation (once daily) group | 19.8 ± 3.2 | 2.6 ± 0.9** | 85.4 |
| 0.2% THY micelle preparation (three times daily) group | 18.4 ± 3.2 | — | 100.0 |

TABLE 8-continued

Effects of THY preparation on ulcer area and ulcer inhibition rate in oral ulcer rats ($\overline{X} \pm SD$, n = 10, ulcer area unit: mm$^2$)

| Groups | 1 d Ulcer area | 9 d Ulcer area | Inhibition rate % |
|---|---|---|---|
| Thickened 0.2% THY micelle preparation (once daily) group | 18.8 ± 3.5 | 2.1 ± 0.7** | 88.8 |
| Thickened 0.2% THY micelle preparation (twice daily) group | 18.1 ± 2.8 | — | 100.0 |
| 0.2% THY CST/THY mixed micelle preparation (once daily) group | 18.6 ± 2.6 | 1.3 ± 0.2** | 93.9 |
| 0.2% THY-Tos CST/THY mixed micelle preparation (once daily) group | 18.8 ± 3.0 | — | 100.0 |
| 0.1 THY and 0.1% THY-Tos CST/THY mixed micelle preparation (once daily) group | 18.9 ± 3.3 | — | 100.0 |
| Guilin Watermelon Frost (once daily) group | 19.2 ± 2.9 | 7.0 ± 1.5** | 61.4 |
| Guilin Watermelon Frost (three times daily) group | 19.3 ± 2.8 | 2.1 ± 0.7** | 88.4 |

Compared with the model group,
*P < 0.05,
**P < 0.01.

Research results were summarized. (1) compared with the model group, the ulcer inhibition rate of the 0.05% THY aqueous solution (once daily) group was 69.8% on the ninth day of administration; and the ulcer inhibition rate of the 0.05% THY aqueous solution (three times daily) group was 87.7% on the ninth day of administration, and the ulcer area was significantly reduced compared with the model group (P<0.01). (2) The ulcer inhibition rates of the 0.05% THY and 0.05% vitamin E aqueous solution (once daily) group and the 0.05% THY-Tos aqueous solution (once daily) group both exceeded 80% on the ninth day of administration, which were better than that of the 0.05% THY aqueous solution (once daily) group, indicating that THY and vitamin E could synergistically act on oral ulcer. (3) The ulcer inhibition rate of the 0.2% THY micelle (once daily) group was 85.4% on the ninth day of administration; and the ulcer inhibition rate in the 0.2% THY micelle preparation (three times daily) group was 100% on the ninth day of administration. The treatment effect of the 0.2% THY micelle preparation (three times) daily group was better than that of the 0.05% THY aqueous solution (three times daily) group on the ninth day of administration. (4) The thickened 0.2% THY micelle solution (twice daily) group could achieve 100% ulcer inhibition rate on the ninth day of administration, indicating that the addition of the thickener to the preparation was helpful to improve the therapeutic effect. (5) The 0.2% THY CST/TPGS mixed micelle preparation (once daily) group and the 0.2% THY-Tos CST/TPGS mixed micelle preparation (once daily) group had good treatment effects, with the ulcer inhibition rate of the former being close to 94% and the ulcer inhibition rate of the latter being 100%, indicating that the mixed micelles improved the drug efficacy by increasing the bioadhesive properties of the preparation on the ulcer surface. (6) The ulcer inhibition rate of the 0.1% THY and 0.1% THY-Tos CST/TPGS mixed micelle preparation (once daily) could be up to 100% on the ninth day of administration. In addition, we noted that the ulcer inhibition rate of the 0.1% THY and 0.1% THY-Tos CST/TPGS mixed micelle preparation (once daily) group was close to 80% on the third day of administration, while the ulcer inhibition rate of the 0.2% THY-Tos CST/TPGS mixed micelle preparation was just over 65% at the same time, indicating that when THY and THY-Tos coexisted, the inhibition on the ulcers was more rapid in the initial stages of administration. (7) Compared with the mixed micelle preparation, the ulcer inhibition rate of the Guilin Watermelon Frost (three times daily) group as a positive drug group was only 88.4% on the ninth day.

The invention claimed is:

1. A micelle preparation, the preparation comprising the following components in parts by weight:
THY 1 to 3 parts
THY-Tos 1 to 3 parts
CST 2 to 3 parts
TPGS 10 to 90 parts
water 1000 parts, wherein
a sum of parts by weight of THY and THY-Tos in the micelle preparation does not exceed one-fifth of a sum of a parts by weight of CST and TPGS;
the THY-Tos has a structural formula (I) as follows:

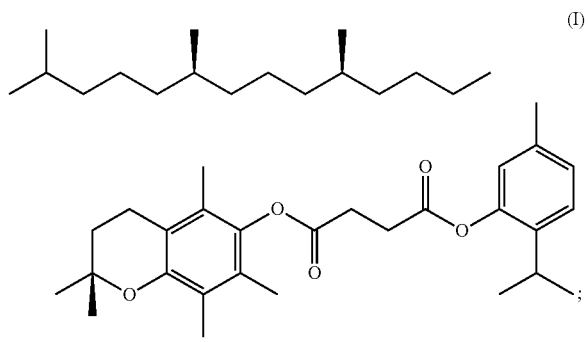

the THY has a structural formula (II) as follows:

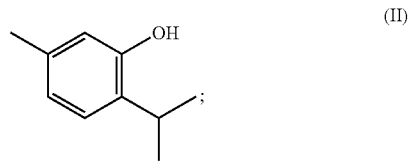

the CST has a structural formula (III) as follows:

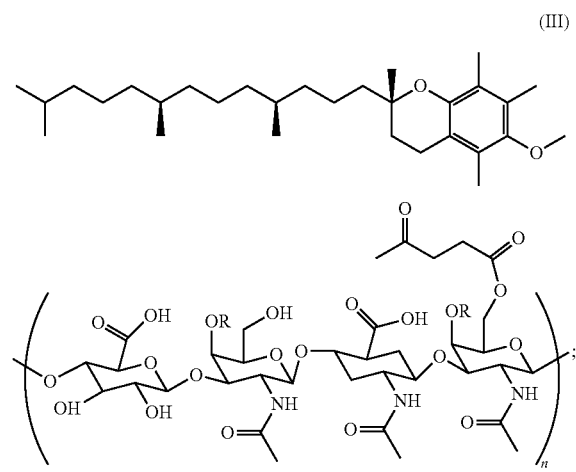

where n=5 to 500, and R=SO$_3$Na; and
the TPGS has a structural formula (IV) as follows:

(IV)

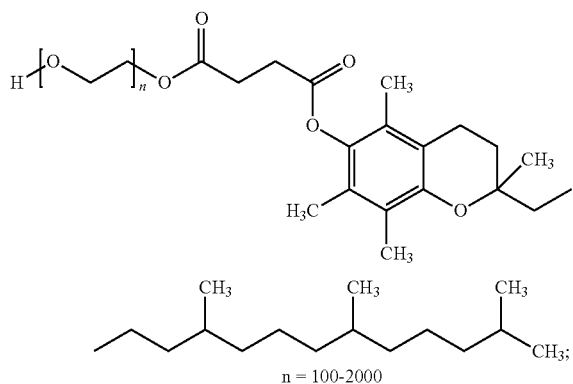

where n=100 to 2000.

2. The micelle preparation according to claim 1, the micelle preparation containing the following components in parts by weight:

THY 1 part
THY-Tos 1 part
CST 2 parts
TPGS 28 parts
purified water 1000 parts.

3. The micelle preparation according to claim 1, the micelle preparation further containing one or more polymer materials selected from the group consisting of carbomer, sodium carboxymethyl cellulose, methyl cellulose, hydroxyethyl cellulose, hydroxypropyl cellulose, hydroxypropyl methyl cellulose.

* * * * *